United States Patent [19]  
van Geem et al.

[11] 4,383,127  
[45] May 10, 1983

[54] OXIDATION OF BENZOIC ACIDS TO PHENOLS

[75] Inventors: Paul C. van Geem, Spaubeek; Antonius J. J. M. Teunissen, Geleen, both of Netherlands

[73] Assignee: Stamicarbon, B.V., Geleen, Netherlands

[21] Appl. No.: 283,148

[22] Filed: Jul. 14, 1981

[51] Int. Cl.$^3$ .............................................. C07C 37/01
[52] U.S. Cl. .................................... 568/801; 252/476
[58] Field of Search ......................... 568/801; 252/476

[56] References Cited

U.S. PATENT DOCUMENTS 2,688,603  9/1954  Baldwin .............................. 252/476
2,727,926  12/1955  Kaeding et al. ..................... 568/801
2,852,567  9/1958  Barnard et al. ..................... 568/801

FOREIGN PATENT DOCUMENTS 719287  10/1965  Canada ............................... 568/801

OTHER PUBLICATIONS

Hackh's, Chemical Dictionary (1969) 433.

Primary Examiner—Bernard Helfin

[57] ABSTRACT

The invention relates to a method for the preparation of a substituted or unsubstituted phenol by oxidation of the corresponding substituted or unsubstituted benzoic acid in the gas phase in the presence of a copper and vanadium and/or silver and lithium and/or sodium and/or magnesium containing catalyst and catalysts therefor. The invention particularly relates to the gas phase oxidation of unsubstituted benzoic acid to unsubstituted phenol.

8 Claims, No Drawings

OXIDATION OF BENZOIC ACIDS TO PHENOLS

The invention relates to a method for the preparation of a substituted or unsubstituted phenol by oxidation of the corresponding substituted or unsubstituted benzoic acid in the gas phase in the presence of a copper containing catalyst and catalysts therefor. The invention particularly relates to the gas phase oxidation of unsubstituted benzoic acid to unsubstituted phenol.

Such a method and catalyst are known from the Dutch patent specification No. 107,561. This patent specification describes such a method and catalyst, in which the catalyst consists of copper oxide on a magnesium oxide carrier. The disadvantage of such a catalyst is that the activity and/or selectivity of it will strongly decrease after a very short time, for instance already after a few hours, so that the application of such a method for the preparation of phenols was economically unattainable.

So far all kinds of attempts have been made to come to an improved catalyst for the above-mentioned method. Thus it was suggested to replace a large part, often even far more than half, of the copper oxide. Such catalysts, however, show faults all of them. Thus no catalyst has so far been known to combine a good activity and selectivity with a long economic life.

The purpose of the invention is to provide a catalyst which does combine these properties.

A method according to the invention is characterized in that, in addition to copper and/or one or more copper compounds, particularly copper oxide, vanadium and/or one or more vanadium compounds and/or silver and/or one or more silver compounds and lithium and/or one or more lithium compounds and/or sodium and or one or more sodium compounds and/or magnesium and or one or more magnesium compounds are applied as catalyst compounds with an atom ratio between vanadium and copper of at most 1:2 and preferably of between 1:250 and 1:10, between silver and copper of at most 1:2 and preferably between 1:500 and 1:4, between lithium and copper of at most 5:1 and preferably of between 1:200 and 2:1, between sodium and copper of at most 5:1 and preferably of between 1:200 and 2:1 and between magnesium and copper of at most 5:1 and preferably of between 1:200 and 2:1 and if both vanadium and silver are present an atom ratio between vanadium and silver preferably of between 1:2 and 25:1, more in particular of between 2:1 and 10:1.

In addition to vanadium and/or silver and lithium and/or sodium and/or magnesium other catalyst compounds may be used as well, c.q. potassium, barium, calcium, cesium, rubidium, strontium, mercury, lead, thallium, arsenic, antimony, chromium, molybdenum, manganese, technetium, rhenium, uranium, the noble metals of group VIII of the Periodic Table of the Elements, the rare earths and one or more compounds containing one or more of these metals.

The catalyst used according to the invention preferably consists of an intimate mixture of CuO and $V_2O_5$ and/or $Ag_2O$ and $Li_2O$ and/or $Na_2O$ and/or MgO and, optionally, one or more other compounds. In addition the catalyst preferably contains 0-95% by weight of carrier material, more specifically 20-80% by weight of carrier material. Preferably a silicon-containing carrier material is applied.

A suitable method of preparation for the catalyst according to the invention is as follows.

The carrier material is suspended in distilled water. Subsequently, at virtually room temperature, for instance 280-320 K, a solution of copper nitrate, a solution of ammonium metavanadate and/or a solution of silvernitrate and, optionally, one or more solutions of one or more cocatalyst metal-containing compounds are added to this suspension.

During firm stirring the metals are precipitated as hydroxide or oxide by adding, in drops, an equivalent quantity of a solution and/or a suspension of lithium and/or sodium and/or magnesium hydroxide. Subsequently the suspension is filtered. The filter cake is broken, dried and, for a certain length of time, for instance 1-50 hours and preferably for 10-25 hours, calcined at a temperature of, for instance, 500-1000 K and preferable of 500-750 K. Finally, the catalyst thus obtained is reduced in size, if necessary, with mechanical means and optionally sieved. The desired catalyst particle size depends on the kind and the size of the particular reactor in which the catalyst particles are applied.

The method according to the invention is carried out as follows.

1 Mole part of substituted or unsubstituted benzoic acid, with 1-100 mole parts of water, for instance in the form of steam, and preferably 5-25 mol parts of water, and 0.05-5 mole parts of oxygen and preferably 0.1-2 mole parts of oxygen, for instance in the form of air, is brought into contact in the gas phase with a catalyst according to the invention at a temperature of 450-700 K, preferably 500-650 K, and at a pressure of preferably 50-2000 kPa, at which higher and lower pressures are not excluded as long as the gas phase is maintained in the reaction medium. Preferably a catalyst load of 0.05-5 parts by weight of substituted or unsubstituted benzoic acid per part by weight of catalyst is applied per hour, specifically 0.1-2 parts by weight of substituted or unsubstituted benzoic acid per part by weight of catalyst per hour. Higher and lower catalyst loads can also be applied, but are, for economic reasons, less attractive.

The gas phase oxidation according to the invention can be effected in all kinds of reactors. Very well applicable are fixed-bed reactors and particularly fluid bed reactors. In a fixed-bed reactor preference is given to the use of catalyst particles with a diameter of between 1 and 10 mm. In a fluid bed reactor preference is given to the use of catalyst particles containing a carrier with a high specific surface, preferably larger than 100 $m^2/g$, more specifically larger than 200 $m^2/g$, and which particles preferably have a diameter of between 20 and 500 $\mu m$.

A very suitable method to carry out the gas phase oxidation according to the invention in a fluid bed reactor is as follows.

The fluidization of the catalyst particles is effected by the supply of oxidizing gas and steam. Thus a fluid bed is formed with a height h. The substituted or unsubstituted benzoic acid to be oxidized is fed, in gaseous state, into the fluid bed at a place separate from the oxidizing gas supply, at a height preferably between $\frac{1}{4}$ and $\frac{3}{4}$ h.

The reaction mixture formed during the gas phase oxidation can be received and condensed. The liquid reaction mixture thus formed can then be separated, as known in the art, into the various components, for instance by distillation. Moreover, instead of ordinary condensation of the reaction gases, fractional condensation can be applied. Thus a separation by distillation can afterwards become superfluous.

The invention also includes catalysts for the catalysis of the gas phase oxidation of substituted or unsubstituted benzoic acid to the corresponding substituted or unsubstituted phenol. These catalysts contain 1000 parts of copper and/or one or more copper compounds, particularly copper oxide, (calculated as Cu atoms) together with 4–100 parts of vanadium and/or one or more vanadium compounds (calculated as V atoms) and/or 2–250 parts of silver and/or one or more silver compounds (calculated as Ag atoms) and 5–2000 parts of lithium and/or one or more lithium compounds (calculated as Li atoms) and/or 5–2000 parts of sodium and/or one or more sodium compounds (calculated as Na atoms) and/or 5–2000 parts of magnesium and/or one or more magnesium compounds (calculated as Mg atoms). These catalysts preferably contain 0–95% by weight of carrier material, more specifically 20–80% by weight of carrier material. Preferably a silicon-containing carrier material is applied. By preference does this carrier material have a specific surface larger than 100 m²/g, more particularly larger than 200 m²/g.

The invention is further elucidated by means of the following non-restrictive examples and comparative experiments.

EXAMPLES AND COMPARATIVE EXPERIMENTS

In the table below examples 1 up to and including 21 and comparative experiments A up to and including G are given. Examples 1 up to and including 20 and comparative experiments A up to and including F have been carried out in a fluid bed reactor as described above, into which reactor the benzoic acid was fed at about ½ h at virtually atmospheric pressure. The example 21 and comparative experiment G have been carried out in a fixed-bed reactor as described above, again at virtually atmospheric pressure.

The load during the experiments was each time about 0.4 g benzoic acid per g catalyst per hour, the molar ratio $H_2O$:benzoic acid about 10:1 to 20:1 and $O_2$:benzoic acid about 0.2.

After 1 hour, 24 hours, 96 hours and 120 hours samples of the reactor gases released were cooled, homogenized with dimethylformamide and analyzed. The results of these analyses are given in the table.

The catalyst used in the gas phase oxidation process had been prepared as described above. In this preparation a calcination time of 16 hours was observed. Besides the metal compounds, the catalyst consisted of Aerosil, a silicon-containing carrier material with a specific surface larger than 200 m²/g.

The table below shows the following:

| Column | I | number of example or comparative experiment |
|---|---|---|
| | II | % by weight of Cu in catalyst |
| | III | % by weight of V in catalyst |
| | IV | % by weight of Ag in catalyst |
| | V | % by weight of Li in catalyst |
| | VI | % by weight of Na in catalyst |
| | VII | % by weight of Mg in catalyst |
| | VIII | duration of the experiment till the measurement in hours |
| | IX | conversion in moles % |
| | X | phenol selectivity in moles % |
| | XI | benzene selectivity in moles % |
| | XII | diphenylether selectivity in moles % |
| | XIII | calcination temperature in K |
| | XIV | reaction temperature in K |

The remainder of the reaction gas consisted of combustion products.

| I | II | III | IV | V | VI | VII | VIII | IX | X | XI | XII | XIII | XIV |
|---|---|---|---|---|---|---|---|---|---|---|---|---|---|
| 1 | 28,3 | 1,2 | | 1,5 | | | 1 | 35,1 | 79,8 | 6,3 | 1,7 | 585 | 570 |
| | | | | | | | 24 | 35,1 | 86,4 | 4,8 | 1,4 | | |
| | | | | | | | 96 | 34,9 | 82,3 | 6,2 | 1,8 | | |
| | | | | | | | 120 | 34,1 | 80,1 | 7,1 | 1,9 | | |
| 2 | 28,7 | 4,0 | | | 1,2 | | 1 | 20,5 | 75,3 | 5,3 | 5,2 | 700 | 540 |
| | | | | | | | 24 | 20,8 | 74,1 | 5,5 | 7,2 | | |
| | | | | | | | 96 | 21,0 | 73,4 | 5,7 | 8,8 | | |
| | | | | | | | 120 | 20,1 | 72,5 | 6,0 | 9,3 | | |
| 3 | 34,0 | 1,8 | | | 0,9 | | 1 | 20,9 | 72,1 | 4,4 | 5,9 | 700 | 540 |
| | | | | | | | 24 | 21,9 | 72,1 | 5,9 | 8,9 | | |
| | | | | | | | 96 | 23,5 | 71,8 | 6,3 | 11,0 | | |
| | | | | | | | 120 | 20,9 | 70,7 | 7,8 | 13,8 | | |
| 4 | 30,1 | 0,6 | | | 9,8 | | 1 | 44,7 | 77,9 | 8,1 | 8,2 | 575 | 540 |
| | | | | | | | 24 | 39,2 | 76,1 | 8,1 | 8,0 | | |
| | | | | | | | 96 | 31,0 | 74,8 | 8,2 | 8,5 | | |
| | | | | | | | 120 | 26,8 | 73,8 | 9,0 | 10,1 | | |
| 5 | 33,6 | 1,8 | | | 0,8 | | 1 | 25,2 | 77,1 | 5,8 | 6,7 | 575 | 540 |
| | | | | | | | 24 | 24,7 | 76,0 | 7,4 | 8,2 | | |
| | | | | | | | 96 | 24,1 | 73,5 | 6,5 | 10,2 | | |
| | | | | | | | 120 | 23,9 | 72,1 | 8,0 | 11,3 | | |
| 6 | 31,2 | 2,0 | | | | 5,8 | 1 | 15,3 | 73,1 | 8,5 | 3,1 | 580 | 570 |
| | | | | | | | 24 | 14,9 | 72,1 | 9,3 | 4,0 | | |
| | | | | | | | 96 | 14,6 | 71,8 | 10,1 | 5,9 | | |
| | | | | | | | 120 | 14,1 | 72,0 | 11,0 | 4,9 | | |
| 7 | 27,4 | | 0,4 | 1,7 | | | 1 | 50,5 | 81,1 | 8,5 | 3,0 | 580 | 575 |
| | | | | | | | 24 | 48,1 | 80,2 | 8,9 | 3,2 | | |
| | | | | | | | 96 | 45,0 | 78,9 | 9,1 | 5,0 | | |
| | | | | | | | 120 | 43,7 | 78,1 | 9,5 | 4,8 | | |
| 8 | 27,6 | | 9,3 | | 4,5 | | 1 | 33,1 | 73,8 | 7,6 | 5,6 | 700 | 555 |
| | | | | | | | 24 | 33,0 | 73,7 | 7,9 | 6,0 | | |
| | | | | | | | 96 | 32,9 | 73,4 | 8,9 | 6,2 | | |
| | | | | | | | 120 | 32,0 | 73,2 | 9,0 | 6,3 | | |
| 9 | 27,6 | | 9,3 | | 4,5 | | 1 | 40,6 | 80,1 | 6,9 | 5,0 | 575 | 555 |
| | | | | | | | 24 | 37,8 | 78,2 | 6,9 | 6,0 | | |
| | | | | | | | 96 | 35,7 | 77,1 | 6,2 | 6,7 | | |
| | | | | | | | 120 | 35,1 | 76,9 | 6,3 | 6,9 | | |
| 10 | 32,0 | | 0,1 | | 3,4 | | 1 | 42,5 | 81,9 | 5,4 | 6,9 | 700 | 575 |
| | | | | | | | 24 | 32,7 | 71,0 | 13,7 | 6,2 | | |

-continued

| I | II | III | IV | V | VI | VII | VIII | IX | X | XI | XII | XIII | XIV |
|---|---|---|---|---|---|---|---|---|---|---|---|---|---|
|   |   |   |   |   |   |   | 96 | 24,8 | 71,1 | 15,1 | 6,3 |   |   |
|   |   |   |   |   |   |   | 120 | 23,2 | 70,1 | 15,3 | 5,8 |   |   |
| 11 | 31,2 |   | 0,3 |   |   | 6,0 | 1 | 18,1 | 80,0 | 8,5 | 5,1 | 580 | 570 |
|   |   |   |   |   |   |   | 24 | 17,3 | 79,1 | 9,1 | 6,0 |   |   |
|   |   |   |   |   |   |   | 96 | 16,3 | 78,0 | 10,0 | 6,1 |   |   |
|   |   |   |   |   |   |   | 120 | 16,1 | 77,1 | 11,0 | 7,0 |   |   |
| 12 | 31,2 | 1,2 | 0,5 | 3,8 |   |   | 1 | 43,7 | 88,6 | 4,0 | 1,9 | 585 | 570 |
|   |   |   |   |   |   |   | 24 | 46,1 | 86,8 | 3,8 | 1,5 |   |   |
|   |   |   |   |   |   |   | 96 | 45,0 | 84,1 | 5,1 | 2,2 |   |   |
|   |   |   |   |   |   |   | 120 | 44,2 | 83,2 | 6,2 | 3,0 |   |   |
| 13 | 30,0 | 1,3 | 0,4 | 1,9 |   |   | 1 | 48,5 | 84,7 | 6,4 | 1,5 | 590 | 570 |
|   |   |   |   |   |   |   | 24 | 47,2 | 87,9 | 4,8 | 1,3 |   |   |
|   |   |   |   |   |   |   | 96 | 47,8 | 83,5 | 6,1 | 2,0 |   |   |
|   |   |   |   |   |   |   | 120 | 46,1 | 84,1 | 7,0 | 2,5 |   |   |
| 14 | 31,8 | 1,1 | 0,3 |   | 1,2 |   | 1 | 21,7 | 80,8 | 4,2 | 7,2 | 575 | 540 |
|   |   |   |   |   |   |   | 24 | 19,3 | 79,8 | 4,5 | 8,3 |   |   |
|   |   |   |   |   |   |   | 96 | 19,7 | 79,5 | 4,6 | 8,3 |   |   |
|   |   |   |   |   |   |   | 120 | 21,4 | 75,8 | 6,2 | 10,1 |   |   |
| 15 | 31,8 | 1,1 | 0,3 |   | 1,2 |   | 1 | 47,5 | 78,8 | 4,3 | 7,0 | 575 | 590 |
|   |   |   |   |   |   |   | 24 | 52,4 | 79,3 | 4,6 | 8,0 |   |   |
|   |   |   |   |   |   |   | 96 | 45,4 | 80,4 | 5,1 | 4,9 |   |   |
|   |   |   |   |   |   |   | 120 | 39,5 | 79,3 | 3,9 | 3,0 |   |   |
| 16 | 33,5 | 0,7 | 0,2 |   | 0,9 |   | 1 | 22,3 | 76,1 | 7,6 | 8,0 | 575 | 565 |
|   |   |   |   |   |   |   | 24 | 21,9 | 75,2 | 10,8 | 7,7 |   |   |
|   |   |   |   |   |   |   | 96 | 21,7 | 74,1 | 12,9 | 7,4 |   |   |
|   |   |   |   |   |   |   | 120 | 21,0 | 72,4 | 14,8 | 6,7 |   |   |
| 17 | 31,1 | 0,4 | 1,1 |   | 1,1 |   | 1 | 15,2 | 75,4 | 3,7 | 8,0 | 575 | 540 |
|   |   |   |   |   |   |   | 24 | 16,2 | 74,9 | 5,2 | 7,8 |   |   |
|   |   |   |   |   |   |   | 96 | 15,1 | 74,7 | 6,1 | 7,6 |   |   |
|   |   |   |   |   |   |   | 120 | 14,9 | 74,3 | 7,1 | 7,2 |   |   |
| 18 | 31,1 | 0,4 | 1,1 |   | 1,1 |   | 1 | 37,1 | 75,2 | 13,8 | 7,5 | 575 | 565 |
|   |   |   |   |   |   |   | 24 | 35,7 | 73,6 | 16,1 | 6,8 |   |   |
|   |   |   |   |   |   |   | 96 | 36,9 | 74,7 | 14,7 | 6,2 |   |   |
|   |   |   |   |   |   |   | 120 | 35,0 | 74,6 | 15,7 | 6,6 |   |   |
| 19 | 32,0 | 1,1 | 0,4 |   |   | 2,0 | 1 | 30,1 | 77,1 | 10,5 | 8,0 | 575 | 590 |
|   |   |   |   |   |   |   | 24 | 30,2 | 78,0 | 11,0 | 7,5 |   |   |
|   |   |   |   |   |   |   | 96 | 29,8 | 77,5 | 10,8 | 8,9 |   |   |
|   |   |   |   |   |   |   | 120 | 27,5 | 77,0 | 10,9 | 9,5 |   |   |
| 20 | 30,6 | 1,3 | 0,4 | 1,2 | 4,3 |   | 1 | 46,7 | 84,4 | 6,6 | 3,3 | 585 | 575 |
|   |   |   |   |   |   |   | 24 | 41,6 | 86,3 | 4,6 | 3,3 |   |   |
|   |   |   |   |   |   |   | 96 | 38,1 | 86,4 | 4,5 | 3,4 |   |   |
|   |   |   |   |   |   |   | 120 | 37,7 | 85,9 | 5,1 | 3,3 |   |   |
| 21 | 30,6 | 1,3 | 0,4 | 1,2 | 4,3 |   | 1 | 32,1 | 81,3 | 4,1 | 5,1 | 585 | 575 |
|   |   |   |   |   |   |   | 24 | 31,6 | 80,1 | 3,6 | 6,0 |   |   |
|   |   |   |   |   |   |   | 96 | 30,5 | 81,2 | 3,9 | 5,9 |   |   |
|   |   |   |   |   |   |   | 120 | 29,8 | 79,5 | 4,2 | 4,8 |   |   |
| A | 30,1 |   |   |   |   |   | 1 | 10,0 | 48,4 | 7,4 | 1,6 | 585 | 540 |
|   |   |   |   |   |   |   | 24 | 5,2 | 36,8 | 7,9 | 5,7 |   |   |
|   |   |   |   |   |   |   | 96 | 3,6 | 30,1 | 8,0 | 10,9 |   |   |
|   |   |   |   |   |   |   | 120 | 3,0 | 25,9 | 8,1 | 12,8 |   |   |
| B | 28,8 |   |   |   | 1,8 |   | 1 | 40,3 | 77,6 | 11,3 | 3,1 | 585 | 575 |
|   |   |   |   |   |   |   | 24 | 31,5 | 75,3 | 13,0 | 2,5 |   |   |
|   |   |   |   |   |   |   | 96 | 25,7 | 70,1 | 18,1 | 3,7 |   |   |
|   |   |   |   |   |   |   | 120 | 20,8 | 61,9 | 22,0 | 5,6 |   |   |
| C | 33,7 |   |   |   |   | 3,9 | 1 | 20,2 | 70,8 | 22,3 | 2,8 | 575 | 540 |
|   |   |   |   |   |   |   | 24 | 20,1 | 60,3 | 28,5 | 3,9 |   |   |
|   |   |   |   |   |   |   | 96 | 19,8 | 51,2 | 35,1 | 5,8 |   |   |
|   |   |   |   |   |   |   | 120 | 19,7 | 35,9 | 40,7 | 8,9 |   |   |
| D | 31,2 |   |   |   |   | 6,0 | 1 | 25,0 | 72,8 | 15,1 | 3,9 | 580 | 565 |
|   |   |   |   |   |   |   | 24 | 21,0 | 67,9 | 17,9 | 4,1 |   |   |
|   |   |   |   |   |   |   | 96 | 18,1 | 60,1 | 25,1 | 5,9 |   |   |
|   |   |   |   |   |   |   | 120 | 17,0 | 55,1 | 30,7 | 8,7 |   |   |
| E | 9,9 | 15,8 |   |   | 4,0 |   | 1 | 6,9 | 43,0 | 6,5 | 0,6 | 700 | 540 |
|   |   |   |   |   |   |   | 24 | 6,1 | 35,1 | 6,4 | 1,3 |   |   |
|   |   |   |   |   |   |   | 96 | 5,4 | 29,7 | 6,6 | 1,9 |   |   |
|   |   |   |   |   |   |   | 120 | 4,8 | 25,1 | 6,7 | 2,6 |   |   |
| F | 10,9 |   |   | 18,8 | 4,0 |   | 1 | 31,9 | 46,5 | 27,4 | 8,4 | 590 | 570 |
|   |   |   |   |   |   |   | 24 | 28,1 | 34,9 | 33,2 | 6,6 |   |   |
|   |   |   |   |   |   |   | 96 | 28,4 | 33,7 | 35,6 | 5,7 |   |   |
|   |   |   |   |   |   |   | 120 | 27,5 | 31,6 | 36,4 | 7,8 |   |   |
| G | 33,7 |   |   |   |   | 3,9 | 1 | 16,2 | 72,3 | 23,1 | 3,7 | 575 | 540 |
|   |   |   |   |   |   |   | 24 | 15,9 | 61,2 | 29,0 | 4,8 |   |   |
|   |   |   |   |   |   |   | 96 | 14,3 | 44,9 | 35,6 | 5,8 |   |   |
|   |   |   |   |   |   |   | 120 | 13,9 | 31,0 | 45,9 | 5,8 |   |   |

We claim:

1. A method for the preparation of a substituted or unsubstitued phenol by the gas phase oxidation of the corresponding substituted or unsubstituted benzoic acid, wherein said oxidation is conducted in the presence of a catalyst system consisting essentially of
   (a) a copper component,
   (b) at least one vanadium or silver component, and (c) at least one lithium, sodium or magnesium component and wherein the atomic ratios of said respective catalyst components (b) and (c) to copper are as follows:
  (i) vanadium and or silver:copper at most 1:2,
  (ii) lithium and or sodium and or magnesium:copper at most 5:1,
under process conditions wherein there is introduced into said gas phase for each 1 mole portion of said benzoic acid,
  1–100 mole portions of water, and
  0.05–5 mole portions of oxygen with said gas phase having a temperature of 450°–700° K. and a pressure of 50–2000 kPa.

2. Method according to claim 1 wherein said atomic ratio of vanadium:copper is between 1:250 and 1:10.

3. Method according to claim 1 wherein said atomic ratio of silver:copper is between 1:500 and 1:4.

4. Method according to claim 1, 2 or 3 wherein said atomic ratio of lithium:copper is between 1:200 and 2:1.

5. Method according to claim 1, 2, or 3 wherein said atomic ratio of sodium:copper is between 1:200 and 2:1.

6. Method according to claim 1, 2 or 3 wherein said atomic ratio of magnesium:copper is between 1:200 and 2:1.

7. Method according to claim 1, 2 or 3 wherein said gas phase oxidation is carried out in a fluid bed reactor.

8. Method according to claim 1, wherein said benzoid acid starting material is introduced into a fluid bed at a height of between ¼ and ¾ parts of the total height of the bed, and separately from the supply for oxygen-containing gas.

* * * * *